United States Patent
Yuchi et al.

(10) Patent No.: US 11,759,177 B2
(45) Date of Patent: Sep. 19, 2023

(54) THREE-DIMENSIONAL ULTRASOUND TOMOGRAPHY METHOD AND SYSTEM BASED ON SPIRAL SCANNING

(71) Applicant: HUAZHONG UNIVERSITY OF SCIENCE AND TECHNOLOGY, Hubei (CN)

(72) Inventors: Ming Yuchi, Hubei (CN); Mingyue Ding, Hubei (CN); Zhaohui Liu, Hubei (CN); Qiude Zhang, Hubei (CN); Junjie Song, Hubei (CN); Shanshan Wang, Hubei (CN); Liang Zhou, Hubei (CN); Kuolin Liu, Hubei (CN)

(73) Assignee: HUAZHONG UNIVERSITY OF SCIENCE AND TECHNOLOGY, Hubei (CN)

( * ) Notice: Subject to any disclaimer, the term of this patent is extended or adjusted under 35 U.S.C. 154(b) by 212 days.

(21) Appl. No.: 17/287,531

(22) PCT Filed: May 15, 2020

(86) PCT No.: PCT/CN2020/090589
§ 371 (c)(1),
(2) Date: Apr. 22, 2021

(87) PCT Pub. No.: WO2021/135039
PCT Pub. Date: Jul. 8, 2021

(65) Prior Publication Data
US 2022/0280136 A1      Sep. 8, 2022

(30) Foreign Application Priority Data

Dec. 31, 2019   (CN) .......................... 201911410149.6

(51) Int. Cl.
*A61B 8/08*     (2006.01)
*A61B 8/00*     (2006.01)
(Continued)

(52) U.S. Cl.
CPC .............. *A61B 8/483* (2013.01); *A61B 8/085* (2013.01); *A61B 8/0825* (2013.01); *A61B 8/145* (2013.01);
(Continued)

(58) Field of Classification Search
CPC ....... A61B 8/483; A61B 8/0825; A61B 8/085; A61B 8/145; A61B 8/4411; A61B 8/5215;
(Continued)

(56) References Cited

FOREIGN PATENT DOCUMENTS

| CN | 105411626   |   | 3/2016 |              |
|----|-------------|---|--------|--------------|
| CN | 105411626 A | * | 3/2016 | ... A61B 6/03 |

OTHER PUBLICATIONS

Liu C, Xue C, Zhang B, Zhang G, He C. The Application of an Ultrasound Tomography Algorithm in a Novel Ring 3D Ultrasound Imaging System. Sensors (Basel). Apr. 25, 2018;18(5):1332. doi: 10.3390/s18051332. PMID: 29693610; PMCID: PMC5982653. (Year: 2018).*

(Continued)

*Primary Examiner* — Boniface Ngathi
*Assistant Examiner* — Zainab Mohammed Aldarraji
(74) *Attorney, Agent, or Firm* — JCIP GLOBAL INC.

(57) ABSTRACT

A three-dimensional ultrasound tomography method and system based on spiral scanning are provided. The method includes the following. (1) Collecting raw data: an emission array element is switched while a probe maintains a uniform linear motion, so that changes in trajectory with time of a position of an equivalent emission array element in a three-dimensional space show a spiral or a partial spiral, and echo data is received. (2) Pre-processing data. (3) Calculating coordinates of each equivalent emission array element. (4) Calculating coordinates of an imaging focus point. (5) Performing synthetic aperture focusing on each imaging (Continued)

focus point. (6) Post-processing data. The disclosure improves the principle of the imaging method, the design of the overall process, etc. Volume data containing information of continuous tissue layers is obtained through spiral scanning. Applying the synthetic aperture focusing technique in the three-dimensional space improves the resolution between layers and shorten the scan time.

6 Claims, 6 Drawing Sheets

(51) Int. Cl.
  *G01S 15/89* (2006.01)
  *A61B 8/14* (2006.01)
(52) U.S. Cl.
  CPC .......... *A61B 8/4411* (2013.01); *A61B 8/5215* (2013.01); *G01S 15/8927* (2013.01); *G01S 15/8993* (2013.01)

(58) Field of Classification Search
  CPC ... A61B 8/5207; A61B 8/0866; A61B 8/5223; A61B 8/4488; G01S 15/8927; G01S 15/8993; G01S 15/892; G01S 15/8945; G01S 15/8997; G01S 15/5207; G01S 15/0866; G01S 15/5223; G01S 15/4488
  See application file for complete search history.

(56) References Cited

OTHER PUBLICATIONS

"International Search Report (Form PCT/ISA/210) of PCT/CN2020/090589," dated Oct. 13, 2020, pp. 1-4.

* cited by examiner

THREE-DIMENSIONAL ULTRASOUND TOMOGRAPHY METHOD AND SYSTEM BASED ON SPIRAL SCANNING

CROSS-REFERENCE TO RELATED APPLICATION

This application is a 371 of international application of PCT application serial no. PCT/CN2020/090589, filed on May 15, 2020, which claims the priority benefit of China application no. 201911410149.6, filed on Dec. 31, 2019. The entirety of each of the above mentioned patent applications is hereby incorporated by reference herein and made a part of this specification.

BACKGROUND

Technical Field

The disclosure relates to the field of ultrasound tomography, and more specifically relates to a three-dimensional ultrasound tomography method and system based on spiral scanning.

Description of Related Art

Ultrasound tomography has the advantages of non-invasiveness, no radiation, high resolution, and high sensitivity, has broad application prospects in the early diagnosis of soft tissue tumors, and has gradually become one of the hotspots in the field of ultrasound applications.

Ultrasound tomography may be divided into reflection imaging and transmission imaging. The transmission imaging contains sound speed reconstruction and attenuation reconstruction. The reflection image shows the structural information of the target, and the sound speed image and the attenuation image show the functional information of the target. The ultrasound tomography system adopts step scanning to obtain information of different tissue regions, and may reconstruct a three-dimensional tissue image.

The Karmanos Cancer Center in the United States has designed a prototype ultrasound tomography system that may obtain a sub-millimeter-level high-resolution image, and is currently in a leading position in the field of early detection of breast cancer. The detector of the system is composed of a ring-shaped array. A large number of array elements are uniformly distributed on the circumference of the detector. Each time a single array element is used to emit an ultrasonic wave to the center of the ring-shaped array, and are received by all array elements until each array element has completed emission. Therefore, a 360-degree scattering signal may be collected for reconstruction of reflection and transmission modes. The system adopts a tomographic scan mode similar to conventional X-ray tomography, and obtains information of discrete tissue layers. Considering the influence of scan time on the result, the interval between the layers is at a millimeter-level. However, the resolution of an ultrasound tomography image has reached sub-millimeter level, which brings difficulties to the subsequent three-dimensional reconstruction.

SUMMARY

In view of the above defects or improvement requirements of the prior art, the objective of the disclosure is to provide a three-dimensional ultrasound tomography method and system based on spiral scanning, which improve the principle of the imaging method, the process design of the overall method, the design of the functional components of the corresponding system, etc. Volume data containing information of continuous tissue layers is obtained through spiral scanning. Applying the synthetic aperture focusing technique in a three-dimensional space is proposed for the first time, which can improve the resolution between layers and shorten the scan time, thereby improving the imaging quality of the system.

To achieve the above objective, according to an aspect of the disclosure, a three-dimensional ultrasound tomography method based on spiral scanning is provided, which includes the following steps.

(1) Collecting raw data:

Array elements in a ring-shaped probe or a partial ring-shaped probe are numbered from 1 to N in the clockwise direction or the counterclockwise direction, where N is the total number of array elements in the probe. The N array elements are uniformly distributed on the probe. Under the premise that the probe maintains a uniform linear motion, an emission array element is switched according to a preset emission rule. Assuming that a motion-emission cycle contains L emission events, and each emission event corresponds to an equivalent emission array element, then the emission event numbered as 1 starts to emit an ultrasonic signal until the emission event numbered as L. The changes in trajectory with time of the position of the equivalent emission array element corresponding to each emission event in the three-dimensional space will show a complete spiral or a partial spiral, so as to complete the motion-emission cycle. In this way, the emission array element is continuously updated to complete multiple motion-emission cycles. For any emission event, while emitting the ultrasonic signal, each array element in the probe receives and collects the ultrasonic signal to obtain raw echo data.

(2) Pre-processing the data:

A filtering process is performed on the raw echo data obtained in Step (1) to obtain a filtered signal.

(3) Calculating the three-dimensional space coordinates of the equivalent emission array element of each emission event in each motion-emission cycle.

(4) Performing voxelization on an imaging area: Voxelization is performed on a three-dimensional imaging area, and three-dimensional space coordinates of each imaging focus point are obtained.

(5) Performing synthetic aperture focusing on each of the imaging focus point: The three-dimensional space coordinates of the equivalent emission element of each emission event obtained in Step (3), and the three-dimensional space coordinates of each of the imaging focus point obtained in Step (4) are used. In the three-dimensional imaging area, based on the principle of synthetic aperture focusing technique, each voxel in the three-dimensional imaging area serves as the imaging focus point for focusing point by point, so as to obtain an echo intensity distribution of each of the imaging focus point. Based on the echo intensity distributions of the imaging focus points, the echo intensity distribution of the overall three-dimensional imaging area may be obtained.

(6) Post processing the data: Filtering, envelope detection, logarithmic compression, and gray-scale mapping are performed on the echo intensity distribution of the overall three-dimensional imaging area obtained in Step (5) to reconstruct a three-dimensional ultrasound tomography image.

As a further preference of the disclosure, Step (5) is specifically:

It is assumed that the total number of emission events is W, and the emission events are numbered from 1 to W. For a certain imaging focus point P in the three-dimensional imaging area, based on the principle of synthetic aperture focusing technique, the three-dimensional space coordinates of the equivalent emission array element of each emission event obtained in Step (3) are used. According to the three-dimensional space coordinates of the equivalent emission array element of the group of W emission events, the echo intensity distribution of the imaging focus point P is calculated. The echo intensity satisfies:

$$I_p = \sum_{i=1}^{W} \sum_{j \in \Omega_i} s_{i,j}(t - \tau_{i,j})$$

where i corresponds to the equivalent emission array element of the i-th emission event in the group of W emission events, $\Omega_i$ is the set composed of sub-aperture receiving array elements corresponding to the i-th emission event, and j represents an array element numbered as j in $\Omega_i$; and $$\tau_{i,j} = \frac{1}{c}(d_{i,TX} + d_{j,RX})$$
$$d_{i,TX} = \sqrt{(x_i - x_p)^2 + (y_i - y_p)^2 + (z_i - z_p)^2}$$
$$d_{j,RX} = \sqrt{(x_j - x_p)^2 + (y_j - y_p)^2 + (z_j - z_p)^2}$$

where $(x_i, y_i, z_i)$ are the three-dimensional space coordinates of the equivalent emission array element of the i-th emission event; $(x_j, y_j, z_j)$ are the three-dimensional space coordinates of a receiving array element when an array element numbered as j in the sub-aperture receiving array element set corresponding to the i-th emission event serves as the receiving array element; $(x_p, y_p, z_p)$ are the three-dimensional space coordinates of the imaging point P; $d_{i,TX}$ is the spatial distance between the equivalent emission array element of the i-th emission event and the imaging point P, and $d_{j,RX}$ is the spatial distance between a receiving array element and the imaging point P when an array element numbered as j in the sub-aperture receiving array element set corresponding to the i-th emission event serves as the receiving array element; c is the pre-selected sound speed value, preferably, c=1540 m/s; $\tau_{i,j}$ is the delay time of a sound wave starting from the equivalent emission element of the i-th emission event, passing through the imaging point P, and then reaching an array element numbered as j in the sub-aperture receiving array element set corresponding to the i-th emission event from the imaging point P when the element serves as the receiving array element; $s_{i,j}(t-\tau_{i,j})$ represents the delay alignment echo signal received by an array element numbered as j in the sub-aperture receiving array element set corresponding to the i-th emission event when the element serves as the receiving array element.

As a further preference of the disclosure, the probe is a ring-shaped probe; and $\Omega_i$ corresponds to a section of continuous array element area on the ring-shaped probe, the area is bilaterally symmetrical with the connecting line between the equivalent emission array element corresponding to the i-th emission event and the center of the ring-shaped probe as the axis of symmetry, and the central angle formed by the area and the center of the ring-shaped probe does not exceed 90°.

As a further preference of the disclosure, in Step (1), the preset emission rule specifically corresponds to:

(i) Each emission event contains only one array element emitting an ultrasonic wave, and the array element corresponds to one equivalent emission array element; or (ii) Each emission event contains multiple adjacent array elements simultaneously emitting ultrasonic waves, and the array elements together correspond to one equivalent emission array element; or (iii) Each emission event contains multiple array elements emitting ultrasonic waves according to the preset delay requirements, and the array elements together correspond to one equivalent emission array element.

As a further preference of the disclosure, in Step (1), when the probe is a ring-shaped probe, any one of the motion-emission cycles corresponds to a complete spiral.

When the probe is a partial ring-shaped probe, any one of the motion-emission cycles corresponds to a partial spiral.

As a further preference of the disclosure, in Step (2), the filtering process specifically removes the direct current component in the raw echo data.

According to another aspect of the disclosure, the disclosure provides a three-dimensional ultrasound tomography system based on spiral scanning, which includes the following.

A raw data collection module is used to: number array elements in a ring-shaped probe or a partial ring-shaped probe from 1 to N in the clockwise direction or the counterclockwise direction, where N is the total number of array elements in the probe, and the N array elements are uniformly distributed on the probe; under the premise that the probe maintains a uniform linear motion, an emission array element is switched according to a preset emission rule, assuming that a motion-emission cycle contains L emission events, and each emission event corresponds to an equivalent emission array element, then the emission event numbered as 1 starts to emit an ultrasonic signal until the emission event numbered as L, and the changes in trajectory with time of the position of the equivalent emission array element corresponding to each emission event in the three-dimensional space will show a complete spiral or a partial spiral, so as to complete the motion-emission cycle; in this way, the emission array element is continuously updated to complete multiple motion-emission cycles; and for any emission event, while emitting the ultrasonic signal, each array element in the probe receives and collects the ultrasonic signal to obtain raw echo data.

A data pre-processing module is used to: filter the raw echo data to obtain a filtered signal.

A three-dimensional space coordinate calculation module of the emission array element is used to: calculate three-dimensional space coordinates of the equivalent emission array element of each emission event in each motion-emission cycle.

A three-dimensional space coordinate calculation module of an imaging focus point is used to: perform voxelization on a three-dimensional imaging area and obtain three-dimensional space coordinates of each imaging focus point.

An image reconstruction module is used to: use the three-dimensional space coordinates of the equivalent emission array element of each emission event and the three-dimensional space coordinates of each of the imaging focus point, in the three-dimensional imaging area, based on the principle of synthetic aperture focusing technique, each voxel in the three-dimensional imaging area serves as the imaging focus point for focusing point by point, so as to obtain an echo intensity distribution of each of the imaging focus point; based on the echo intensity distributions of the imaging focus points, the echo intensity distribution of the overall three-dimensional imaging area may be obtained; and filtering, envelope detection, logarithmic compression, and gray-scale mapping are performed on the echo intensity distribution of the overall three-dimensional imaging area to reconstruct a three-dimensional ultrasound tomography image.

Compared with the prior art, the above technical solutions conceived by the disclosure can achieve the following beneficial effects:

The spiral scanning adapted by the three-dimensional ultrasound tomography reconstruction method based on spiral scanning and the corresponding system of the disclosure obtains the volume data containing information of continuous layers, shortens the scan time, and theoretically can reconstruct images of any layer. The current step scanning used in ultrasound tomography can only obtain information of discrete tissue layers, and each scanning process is independent. As such, layers between a series of reconstructed tomography images need to be processed by interpolation to be displayed in three dimensions, which causes low resolution between image layers. However, spiral scanning can obtain the volume data containing information of continuous tissue layer. The resolution between layers may be set according to actual requirements. The reconstruction is directly performed in the three-dimensional space. The model is more compliant with the actual situation. While improving the resolution between layers, the quality of tomography images can also be theoretically improved.

Compared with step scanning, the spiral scanning probe in the disclosure maintains a uniform linear motion. Spiral scanning can shorten the overall scan time (of course, the specific linear motion speed may be flexibly preset according to actual requirements), thereby effectively reducing errors due to breathing and motion, which facilitates subsequent reconstruction of more accurate images.

Compared with spiral trajectory scanning performed by a single array element probe, the ring-shaped array probe in the disclosure can obtain the echo signals sampled at different spatial positions in each emission event. Focus imaging may be performed at both the emission and receiving ends to obtain results of high signal-to-noise ratio and high contrast. Also, the synthesized emission aperture is distributed in the three-dimensional space to obtain higher spatial sampling.

DETAILED DESCRIPTION OF DISCLOSED EMBODIMENTS

Figure 1:
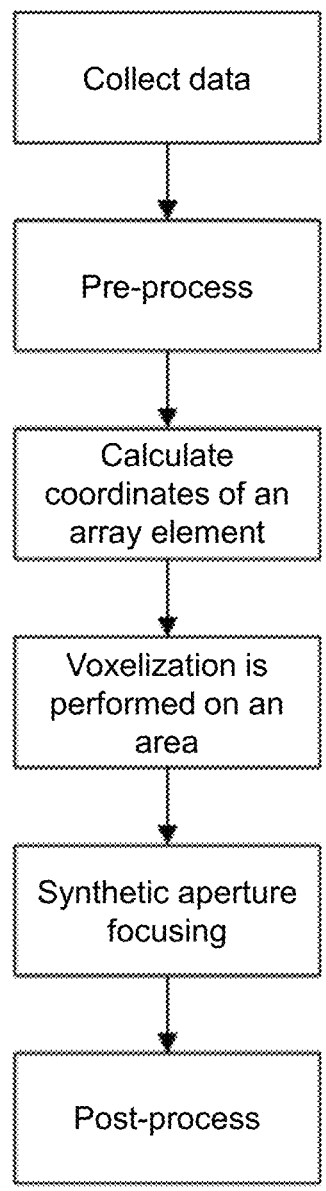
FIG. 1 is a schematic diagram of a flowchart of a three-dimensional ultrasound tomography method based on spiral scanning according to the disclosure.

In order for the objectives, technical solutions, and advantages of the disclosure to be more comprehensible, the following further describes the disclosure in detail with reference to the accompanying drawings and embodiments. It should be understood that the specific embodiments described herein are only used to explain the disclosure, but not to limit the disclosure. In addition, the technical features involved in the various embodiments of the disclosure described below may be combined with each other as long as there is no conflict therebetween.

Generally speaking, the three-dimensional ultrasound tomography method based on spiral scanning of the disclosure includes the following steps.

(1) Collecting data: A ring-shaped or partial ring-shaped array moves at a constant speed. Each array element is sequentially emitted. Relative to an imaging object, the trajectories of all array elements constitute a spiral or a partial spiral. The array elements may be emitted at equal intervals, multiple adjacent array elements may be emitted at the same time, corresponding delay is applied to multiple array elements to constitute a virtual emission array element, or other manners. The specific emission rule (that is, the switching rule of the emission array element) may be preset.

(2) Pre-processing the data: The collected raw echo signal is filtered, or the direct current component is directly removed for subsequent focus reconstruction.

(3) Coordinates of each emission event are calculated: The coordinates of each emission element or synthesized virtual array element are calculated according to array parameters and the motion speed.

(4) Performing voxelization on an imaging area: Voxelization is performed on a limited imaging area to obtain coordinates of an imaging focus point.

(5) Performing synthetic aperture focusing on each of the imaging focus point: In a three-dimensional space, the synthetic aperture focusing technique is used to obtain an echo intensity distribution of each of the imaging focus point.

(6) Post processing the data: Filtering, envelope detection, logarithmic compression, and gray-scale mapping are performed on an obtained focus result. A three-dimensional ultrasound tomography image is finally obtained, which is imported into a three-dimensional reconstruction software for display.

Embodiment 1

The three-dimensional ultrasound tomography method based on spiral scanning in the embodiment specifically includes the following steps.

(1) Collecting data:

Uniformly distributed array elements on a ring detector are numbered from 1 to N, where N is the number of array elements in the detector. A period of time before starting the collection, the detector is drawn by a motor for uniform motion (the direction of motion is defined as parallel to the Z-axis direction of a spatial three-dimensional direct coordinate system), and the speed is denoted as S. When the collection is started, an array element 1 emits an ultrasonic wave, is received by all N array elements. After a time interval T, an array element 2 emits an ultrasonic wave, and is received by all N array elements. Sequentially, after an array element N has emitted, it cycles back to the array element 1 to emit an ultrasonic wave until a scanning area covers an imaging object, and scanning is stopped.

(2) Pre-processing the data:

A filtering process is performed on the raw echo data obtained in Step (1) to eliminate the direct current component and a part of the noise in the signal. A filtered data set is obtained for subsequent reconstruction in Step (5).

Figure 2:
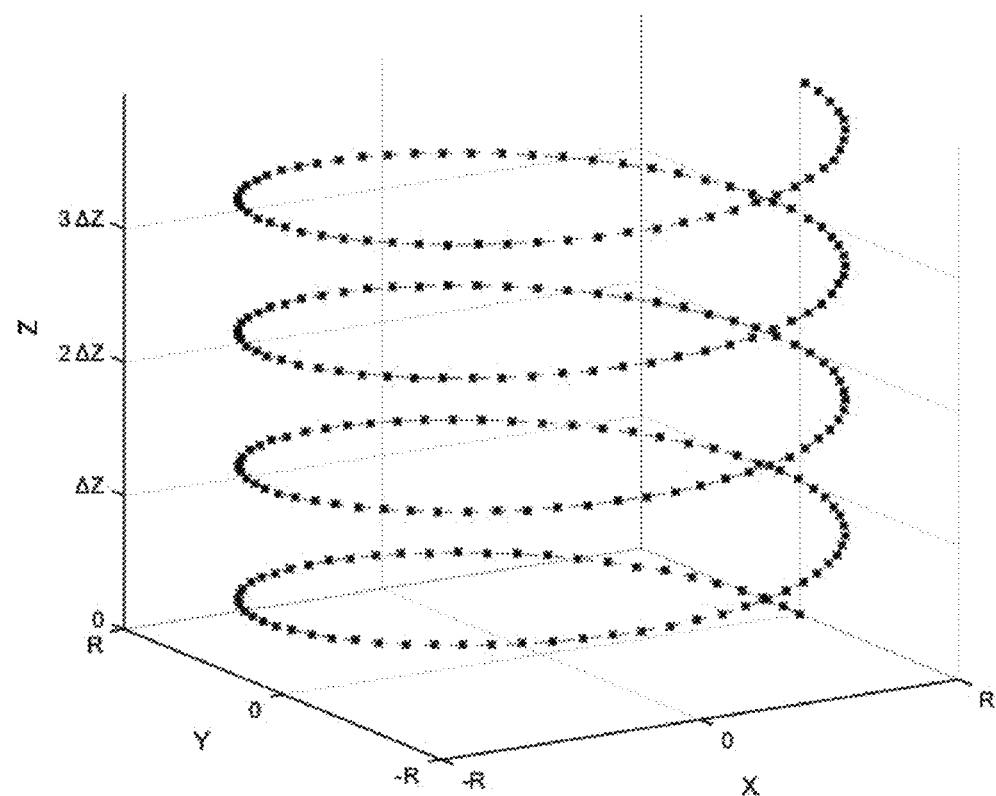
FIG. 2 is a schematic diagram of coordinate distribution of an emission event in Embodiment 1.

(3) Calculating the coordinates of each emission array element:

As shown in FIG. 2, the trajectory formed by all emission array element is a spiral, and the radius thereof is equal to the radius of the detector and is denoted as R. One emission cycle is referred as all array elements in the detector sequentially emitting once. It may be found that coordinates of corresponding array elements in two adjacent emission cycles satisfy the following relationship:

$$x_{k+1,m} = x_{k,m}$$

$$y_{k+1,m} = y_{k,m}$$

$$z_{k+1,m} = z_{k,m}$$

where $(x_{k,m}, y_{k,m}, z_{k,m})$ are the three-dimensional space coordinates of an array element numbered as m in the k-th emission cycle, and $\Delta Z = N \times T \times S$ is the distance moved by the detector under the duration of one emission cycle.

Therefore, it is only necessary to calculate the coordinates of all array elements in one emission cycle, and the coordinates of the remaining emission array element may be derived from the above relationship. The plane where the N array elements of the ring detector are at is defined as parallel to an XOY plane of the three-dimensional direct coordinate system. The center of the ring detector moves along the Z-axis of the three-dimensional direct coordinate system, and three-dimensional space coordinates of the array element numbered as 1 in the first emission cycle when the array element numbered as 1 serves as an emission array element are (R, 0, 0). The following shows that the space coordinates when all array elements in the first emission cycle serve as the emission array element satisfy:

$$x_{1,m} = R \times \cos[(m-1) \times \Delta\theta]$$

$$y_{1,m} = R \times \sin[(m-1) \times \Delta\theta]$$

$$z_{1,m} = (m-1) \times T \times S$$

where $$\Delta\theta = \frac{2\pi}{N}$$

is the central angle angular interval between adjacent array elements; and the value of m is from 1 to N.

(4) Performing voxelization on an imaging area:

Assuming that M emission cycles are actually required to cover the imaging object, then the imaging area may be limited to a cuboid with length, width, and height being respectively $2 \times R$, $2 \times R$, and $\Delta Z \times M$. According to actual requirements, the cuboid area is divided into $A \times A \times H$ voxels, that is, the imaging focus point.

Figure 3:
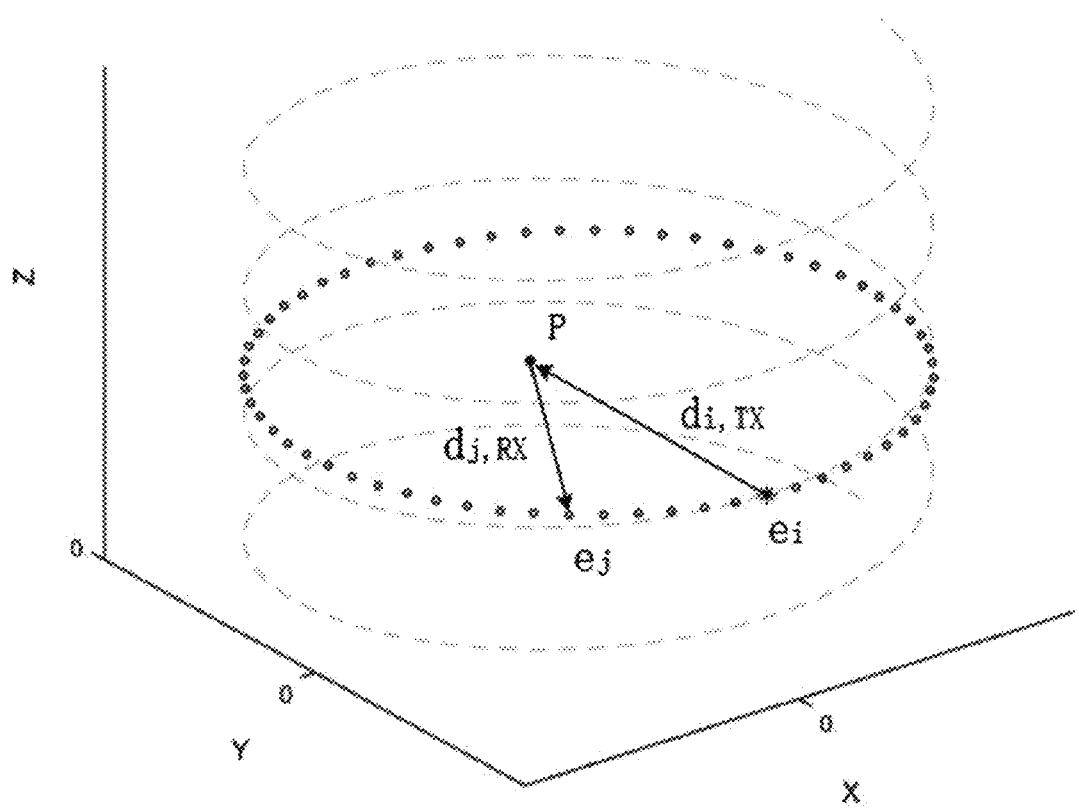
FIG. 3 is a schematic diagram of three-dimensional focusing of an imaging point P in Embodiment 1.

(5) Performing synthetic aperture focusing on each of the imaging focus point:

As shown in FIG. 3, for a certain focus point P in the imaging area, the signal value of the point is given by the following formula:

$$I_p = \sum_{i=1}^{W} \sum_{j \in \Omega_i} s_{i,j}(t - \tau_{i,j})$$

where W is the total number of emission events in the overall scanning process (W may be preset according to the length of the target imaging area, the speed of the linear uniform motion of the probe, the time interval between 2 adjacent emission events, etc.), i corresponds to the emission element emitting at the i-th time (the emission element is also the equivalent emission element of the i-th emission event); and $\Omega_i$ is the set composed of sub-aperture receiving array elements corresponding to the i-th emission event. In the embodiment, corresponds to the set constituting of receiving array elements that are symmetrically distributed with the emission array element as the center and with the corresponding central angle not larger than 90° (the angle may be preset, as long as the angle does not exceed 90°, for example, the angle may be) 90°. The array elements in the set $\Omega_i$ mainly receive backscattered signals from the imaging object, are relatively close to the emission array element, and are used for reconstruction of a reflection image.

$$\tau_{i,j} = \frac{1}{c}(d_{i,TX} + d_{j,RX})$$

$$d_{i,TX} = \sqrt{(x_i - x_p)^2 + (y_i - y_p)^2 + (z_i - z_p)^2}$$

$$d_{j,RX} = \sqrt{(x_j - x_p)^2 + (y_j - y_p)^2 + (z_j - z_p)^2}$$

where $(x_i, y_i, z_i)$ are the three-dimensional space coordinates of the emission array element of the i-th emission event; $(x_j, y_j, z_j)$ are the three-dimensional space coordinates of a receiving array element when an array element numbered as j in the sub-aperture receiving array element set corresponding to the i-th emission event serves as the receiving array element; $(x_p, y_p, z_p)$ are the three-dimensional space coordinates of the imaging point P; $d_{i,TX}$ is the spatial distance between the emission array element of the i-th emission event and the imaging point P, and $d_{j,RX}$ is the spatial distance between a receiving array element and the imaging point P when an array element numbered as j in the sub-aperture receiving array element set corresponding to the i-th emission event serves as the receiving array element; c is the pre-selected sound speed value; $\tau_{i,j}$ is the delay time of a sound wave emitting from the emission element of the i-th emission event, passing through the imaging point P, and then reaching an array element numbered as j in the sub-aperture receiving array element set corresponding to the i-th emission event from the imaging point P when the element serves as the receiving array element; and $s_{i,j}(t-\tau_{i,j})$ represents the delay alignment echo signal received by an array element numbered as j in the sub-aperture receiving array element set corresponding to the i-th emission event when the element serves as the receiving array element.

c is a constant, and is the sound speed in the soft tissue, such as 1540 m/s.

(6) Post processing the data:

The post-processing of the focus result may mainly include steps such as filtering, envelope detection, logarithmic compression, and gray-scale mapping to implement the reconstruction of a three-dimensional ultrasound tomography image. The steps may be performed according to known processing manners in the prior art. For example:

Filtering: In order to reduce the impact of speckle noise on image quality in ultrasonic reflection imaging, a median filter may be used to process focus data. The size of the observation window is related to the number of focus points set.

Envelope detection: In medical ultrasound imaging, the main method used to obtain the signal envelope is to perform Hilbert transform on the signal, so as to obtain an analytical representation of the corresponding signal. The amplitude of the analytical signal is the desired envelope.

Logarithmic compression: Logarithmic operation is performed on the envelope signal to compress the dynamic range of the signal to an ideal range for display, which is generally adjusted to 50 to 70 dB.

Gray-scale mapping: The value of each focus point is linearly mapped to a gray-scale value of 0 to 255, that is, proportionally maps the weakest signal to 0 and the strongest signal to 255 for display in a display.

Finally, the reconstructed three-dimensional ultrasound tomography image may be imported into a three-dimensional reconstruction software for display.

Embodiment 2

The three-dimensional ultrasound tomography method based on spiral scanning in the embodiment specifically includes the following steps.

(1) Collecting data:

It is assumed that the central angle corresponding to the arc of a part of the ring detector is $\theta_0$, and the radius of the arc is R. Uniformly distributed array elements on the part of the ring detector are numbered from 1 to N, where N is the number of array elements in the detector. A period of time before starting the collection, the detector is drawn by a motor for uniform motion (the direction of motion is defined as parallel to the Z-axis direction of a spatial three-dimensional direct coordinate system), and the speed is denoted as S. When the collection is started, an array element 1 emits an ultrasonic wave, and is received by all N array elements. After a time interval T, an array element 2 emits an ultrasonic wave, and is received by all N array elements. Sequentially, after an array element N has emitted, it cycles back to the array element 1 to emit an ultrasonic wave until a scanning area covers an imaging object, and scanning is stopped.

(2) Pre-processing the data:

A filtering process is performed on the raw echo data obtained in Step (1) to eliminate the direct current component and a part of the noise in the signal. A filtered data set is obtained for subsequent reconstruction in Step (5).

Figure 4:
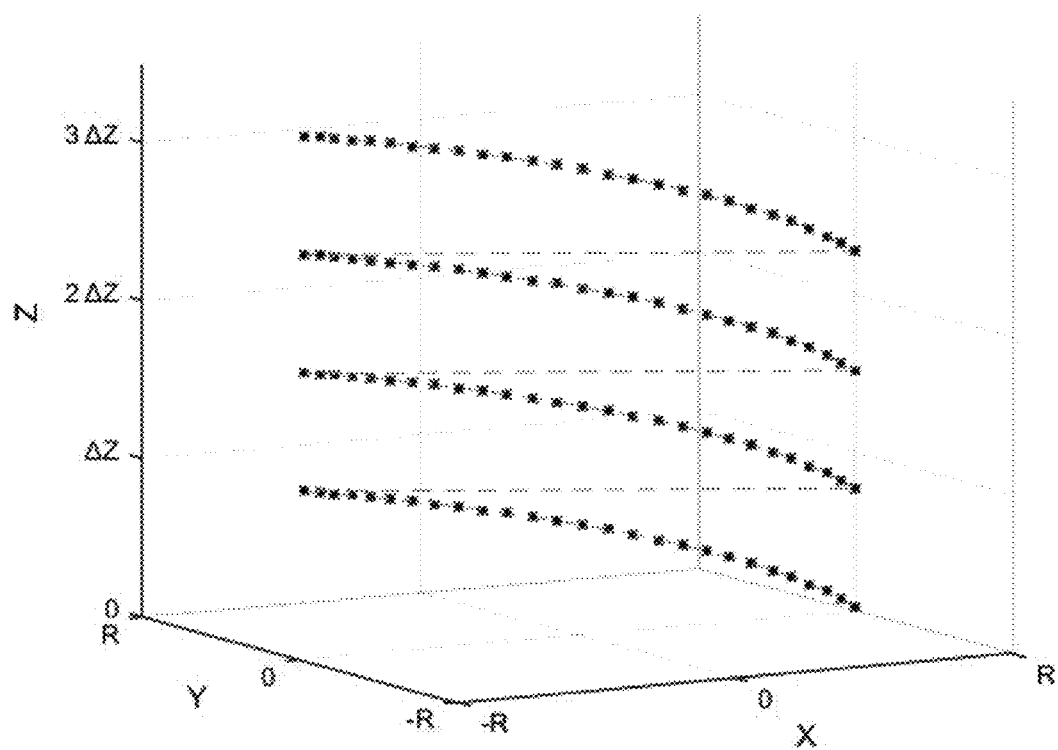
FIG. 4 is a schematic diagram of coordinate distribution of an emission event in Embodiment 2.

(3) Calculating the coordinates of each emission array element:

As shown in FIG. 4, the trajectory formed by all emission array element is an approximate spiral (each cycle corresponds to a partial spiral rather than a complete spiral), and the radius thereof is equal to the radius of the detector and is denoted as R. One emission cycle is referred as all array elements in the detector sequentially emitting once. It may be found that coordinates of corresponding array elements in two adjacent emission cycles satisfy the following relationship:

$$x_{k+1,m} = x_{k,m}$$

$$y_{k+1,m} = y_{k,m}$$

$$z_{k+1,m} = z_{k,m}$$

where $(x_{k,m}, y_{k,m}, z_{k,m})$ are the three-dimensional space coordinates of an array element numbered as m in the k-th emission cycle, and $\Delta Z = N \times T \times S$ is the distance moved by the detector under the duration of one emission cycle.

Therefore, it is only necessary to calculate the coordinates of all array elements in one emission cycle, and the coordinates of the remaining emission array element may be derived from the above relationship. The plane where the N array elements of the ring detector are at is defined as parallel to an XOY plane of the three-dimensional direct coordinate system. The center of the ring detector moves along the Z-axis of the three-dimensional direct coordinate system, and three-dimensional space coordinates of the array element numbered as 1 in the first emission cycle when the array element numbered as 1 serves as an emission array element are (R, 0, 0). The following shows that the space coordinates when all array elements in the first emission cycle serve as the emission array element satisfy: emission cycle serve as the emission array element satisfy:

$$x_{1,m} = R \times \cos[(m-1) \times \Delta\theta]$$

$$y_{1,m} = R \times \sin[(m-1) \times \Delta\theta]$$

$$z_{1,m} = (m-1) \times T \times S$$

where $$\Delta\theta = \frac{2\pi}{N-1}$$

is the central angle angular interval between adjacent array elements; and the value of m is from 1 to N.

(4) Performing voxelization on an imaging area:

Assuming that M emission cycles are actually required to cover the imaging object, then the imaging area may be limited to a cuboid with length, width, and height being respectively $$2 \times R \times \sin\frac{\theta_c}{2},$$

D, and $\Delta Z \times M$. According to actual requirements, a suitable imaging depth D is selected, and the cuboid area is divided into $A \times A \times H$ voxels, that is, the imaging focus point.

(5) Performing synthetic aperture focusing on each of the imaging focus point:

Similar to FIG. 3, for a certain focus point P in the imaging area, the signal value of the point is given by the following formula:

$$I_p = \sum_{i=1}^{W} \sum_{j \in \Omega_i} s_{i,j}(t - \tau_{i,j})$$

where W is the total number of emission events in the overall scanning process, i corresponds to the emission element emitting at the i-th time (the emission element is also the equivalent emission element of the i-th emission event); and $\Omega_i$ is the set composed of sub-aperture receiving array elements corresponding to the i-th emission event. In the embodiment, the selection of $\Omega_i$ may be appropriately determined according to the size of the central angle corresponding to the probe and the depth of the imaging area. For example, in the embodiment, $\Omega_i$ corresponds to the set constituting of receiving array elements that are symmetrically distributed with the emission array element as the center and with the central angle of 45°. Considering that the probe adopted by the embodiment is a partial ring-shaped probe, when there is no array element in some areas in the central angle range of 45°, only the area containing the array elements in the central angle of 45° may be selected. For example, for the leftmost emission array element, the receiving array element set at this time is the set composed of array elements that correspond to the central angle range of 22.5° from the emission array element to the right. For another example, for a certain emission array element with a central angle of 5° to the center of the probe with reference to the leftmost array element of the probe, the receiving array element set at this time is the set composed of array elements starting from the emission array element and in the range of respectively taking the corresponding central angle of 5° to the left (that is, taking the leftmost array element) and taking the corresponding central angle of 22.5° to the right. The array elements in the set $\Omega_i$ mainly receive backscattered signals from the imaging object, are relatively close to the emission array element, and are used for reconstruction of a reflection image.

$$\tau_{i,j} = \frac{1}{c}(d_{i,TX} + d_{j,RX})$$

$$d_{i,TX} = \sqrt{(x_i - x_p)^2 + (y_i - y_p)^2 + (z_i - z_p)^2}$$

$$d_{j,RX} = \sqrt{(x_j - x_p)^2 + (y_j - y_p)^2 + (z_j - z_p)^2}$$

where $(x_i, y_i, z_i)$ are the three-dimensional space coordinates of the emission array element of the i-th emission event; $(x_j, y_j, z_j)$ are the three-dimensional space coordinates of a receiving array element when an array element numbered as j in the sub-aperture receiving array element set corresponding to the i-th emission event serves as the receiving array element; $(x_p, y_p, z_p)$ are the three-dimensional space coordinates of the imaging point P; $d_{i,Tx}$ is the spatial distance between the emission array element of the i-th emission event and the imaging point P, and $d_{j,RX}$ is the spatial distance between a receiving array element and the imaging point P when an array element numbered as j in the sub-aperture receiving array element set corresponding to the i-th emission event serves as the receiving array element; c is the pre-selected sound speed value; $\tau_{i,j}$ is the delay time of a sound wave emitting from the emission element of the i-th emission event, passing through the imaging point P, and then reaching an array element numbered as j in the sub-aperture receiving array element set corresponding to the i-th emission event from the imaging point P when the element serves as the receiving array element; and $s_{i,j}(t-\tau_{i,j})$ represents the delay alignment echo signal received by an array element numbered as j in the sub-aperture receiving array element set corresponding to the i-th emission event when the element serves as the receiving array element.

c is a constant, and is the sound speed in the soft tissue, such as 1540 m/s.

(6) Post processing the data:

The post-processing of the focus result may mainly include steps such as filtering, envelope detection, logarithmic compression, and gray-scale mapping to implement the reconstruction of a three-dimensional ultrasound tomography image. The steps may be performed according to known processing manners in the prior art. For example:

Filtering: In order to reduce the impact of speckle noise on image quality in ultrasonic reflection imaging, a median filter may be used to process focus data. The size of the observation window is related to the number of focus points set.

Envelope detection: In medical ultrasound imaging, the main method used to obtain the signal envelope is to perform Hilbert transform on the signal, so as to obtain an analytical representation of the corresponding signal. The amplitude of the analytical signal is the desired envelope.

Logarithmic compression: Logarithmic operation is performed on the envelope signal to compress the dynamic range of the signal to an ideal range for display, which is generally adjusted to 50 to 70 dB.

Gray-scale mapping: The value of each focus point is linearly mapped to a gray-scale value of 0 to 255, that is, proportionally maps the weakest signal to 0 and the strongest signal to 255 for display in a display.

Finally, the reconstructed three-dimensional ultrasound tomography image may be imported into a three-dimensional reconstruction software for display.

Embodiment 3

The three-dimensional ultrasound tomography method based on spiral scanning in the embodiment specifically includes the following steps.

(1) Collecting data:

Uniformly distributed array elements on a ring detector are numbered from 1 to N, where N is the number of array elements in the detector. A period of time before starting the collection, the detector is drawn by a motor for uniform motion (the direction of motion is defined as parallel to the Z-axis direction of a spatial three-dimensional direct coordinate system), and the speed is denoted as S. After the collection is started, an array element 1 and an array element 2 emit ultrasonic waves at the same time, and is received by all N array elements. After a time interval T, an array element 3 and an array element 4 emit ultrasonic waves, and is received by all N array elements. Sequentially, after all emissions are completed, it cycles back to the array element 1 and the array element 2 to emit ultrasonic waves until a scanning area covers an imaging object, and scanning is stopped. Under such situation, one motion-emission cycle contains N/2 emission events, that is, L=N/2.

Figure 5:
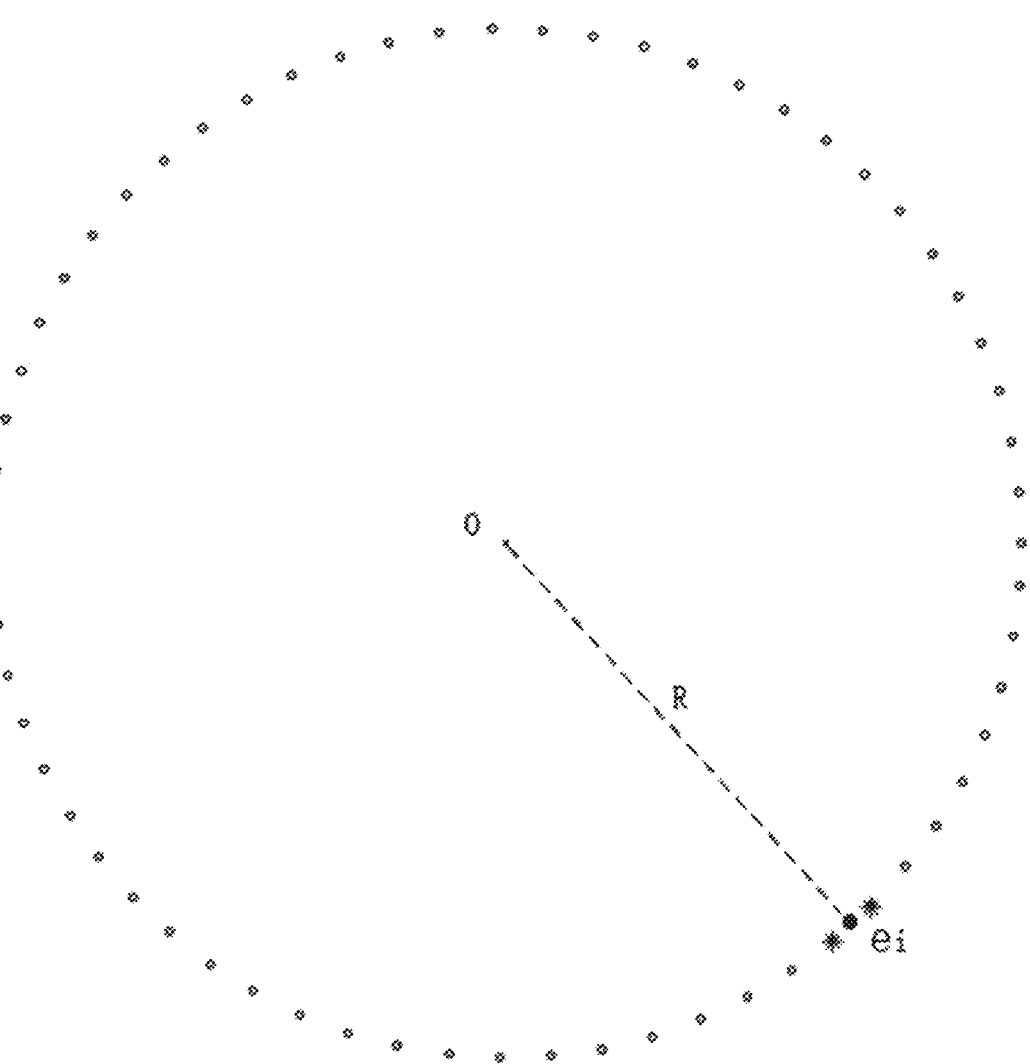
FIG. 5 is a schematic diagram of coordinate distribution of an emission event in Embodiment 3.

In the embodiment, since each emission event corresponds to 2 emission array elements, the 2 emission array elements correspond to one equivalent emission array element. The equivalent emission array element, as shown in FIG. 5, has a circular shape along the ring-shaped probe, is located in the middle of the 2 emission array elements, and is equidistant from the 2 emission array elements.

(2) Pre-processing the data:

A filtering process is performed on the raw echo data obtained in Step (1) to eliminate the direct current component and a part of the noise in the signal. A filtered data set is obtained for subsequent reconstruction in Step (5).

(3) Calculating the coordinates of each emission event:

As shown in FIG. 5, since two adjacent array elements emit ultrasonic waves at the same time, the trajectory formed by all emission array elements emitting at this time is a spiral, and the radius thereof is equal to the radius of the detector and is denoted as R. One emission cycle is referred as all array elements in the detector sequentially emitting once. It may be found that coordinates of corresponding array elements in two adjacent emission cycles satisfy the following relationship:

$$x_{k+1,m} = x_{k,m}$$

$$y_{k+1,m} = y_{k,m}$$

$$z_{k+1,m} = z_{k,m}$$

where $(x_{k,m}, y_{k,m}, z_{k,m})$ are the three-dimensional space coordinates of an equivalent emission array element assumed to be m in the k-th emission cycle, and $\Delta Z = L \times T \times S$ is the distance moved by the detector under the duration of one emission cycle.

Therefore, it is only necessary to calculate the coordinates of all equivalent emission array elements in one emission cycle, and the coordinates of the equivalent emission array elements in the remaining cycles may be derived from the above relationship. The plane where the N array elements of the ring detector are at is defined as parallel to an XOY plane of the three-dimensional direct coordinate system. The center of the ring detector moves along the Z-axis of the three-dimensional direct coordinate system, and three-dimensional space coordinates of the equivalent emission array element of the 1-st emission event in the first emission cycle are (R, 0, 0). The following shows that the space coordinates of all equivalent emission array elements in the first emission cycle satisfy:

$$x_{1,m} = R \times \cos[(m-1) \times \Delta\theta]$$

$$y_{1,m} = R \times \sin[(m-1) \times \Delta\theta]$$

$$z_{1,m} = (m-1) \times T \times S$$

where $$\Delta\theta = \frac{2\pi}{L}$$

is the central angle angular interval between adjacent equivalent emission array elements; and the value of m is from 1 to L.

(4) Performing voxelization on an imaging area:

Assuming that M emission cycles are actually required to cover the imaging object, then the imaging area may be limited to a cuboid with length, width, and height being respectively 2×R, 2×R, and Δz×M. According to actual requirements, the cuboid area is divided into A×A×H voxels, that is, the imaging focus point.

(5) Performing synthetic aperture focusing on each of the imaging focus point:

Similar to FIG. 3, for a certain focus point P in the imaging area, the signal value of the point is given by the following formula:

$$I_p = \sum_{i=1}^{W} \sum_{j \in \Omega_i} s_{i,j}(t - \tau_{i,j})$$

where W is the total number of emission events in the overall scanning process, i corresponds to the emission element emitting at the i-th time (the emission element is also the equivalent emission element of the i-th emission event), and $\Omega_i$ is the set composed of sub-aperture receiving array elements corresponding to the i-th emission event. In the embodiment, $\Omega_i$ corresponds to the set constituting of receiving array elements that are symmetrically distributed with the equivalent emission array element as the center and with the corresponding central angle not larger than 90° (the angle may be preset, as long as the angle does not exceed 90°, for example, the angle may be 90°). The array elements in the set mainly receive backscattered signals from the imaging object, are relatively close to the emission array element, and are used for reconstruction of a reflection image.

$$\tau_{i,j} = \frac{1}{c}(d_{i,TX} + d_{j,RX})$$

$$d_{i,TX} = \sqrt{(x_i - x_p)^2 + (y_i - y_p)^2 + (z_i - z_p)^2}$$

$$d_{j,RX} = \sqrt{(x_j - x_p)^2 + (y_j - y_p)^2 + (z_j - z_p)^2}$$

where $(x_i, y_i, z_i)$ are the three-dimensional space coordinates of the equivalent emission array element of the i-th emission event; $(x_j, y_j, z_j)$ are the three-dimensional space coordinates of a receiving array element when an array element numbered as j in the sub-aperture receiving array element set corresponding to the i-th emission event serves as the receiving array element; $(x_p, y_p, z_p)$ are the three-dimensional space coordinates of the imaging point P; $d_{i,TX}$ is the spatial distance between the equivalent emission array element of the i-th emission event and the imaging point P, and $d_{j,RX}$ is the spatial distance between a receiving array element and the imaging point P when an array element numbered as j in the sub-aperture receiving array element set corresponding to the i-th emission event serves as the receiving array element; c is the pre-selected sound speed value; $\tau_{i,j}$ is the delay time of a sound wave emitting from the emission element of the i-th emission event, passing through the imaging point P, and then reaching an array element numbered as j in the sub-aperture receiving array element set corresponding to the i-th emission event from the imaging point P when the element serves as the receiving array element; and $s_{i,j}(t-\tau_{i,j})$ represents the delay alignment echo signal received by an array element numbered as j in the sub-aperture receiving array element set corresponding to the i-th emission event when the element serves as the receiving array element.

c is a constant, and is the sound speed in the soft tissue, such as 1540 m/s.

(6) Post processing the data:

The post-processing of the focus result may mainly include steps such as filtering, envelope detection, logarithmic compression, and gray-scale mapping to implement the reconstruction of a three-dimensional ultrasound tomography image. The steps may be performed according to known processing manners in the prior art. For example:

Filtering: In order to reduce the impact of speckle noise on image quality in ultrasonic reflection imaging, a median filter may be used to process focus data. The size of the observation window is related to the number of focus points set.

Envelope detection: In medical ultrasound imaging, the main method used to obtain the signal envelope is to perform Hilbert transform on the signal, so as to obtain an analytical representation of the corresponding signal. The amplitude of the analytical signal is the desired envelope.

Logarithmic compression: Logarithmic operation is performed on the envelope signal to compress the dynamic range of the signal to an ideal range for display, which is generally adjusted to 50 to 70 dB.

Gray-scale mapping: The value of each focus point is linearly mapped to a gray-scale value of 0 to 255, that is, proportionally maps the weakest signal to 0 and the strongest signal to 255 for display in a display.

Finally, the reconstructed three-dimensional ultrasound tomography image may be imported into a three-dimensional reconstruction software for display.

Embodiment 4

The three-dimensional ultrasound tomography method based on spiral scanning in the embodiment specifically includes the following steps.

(1) Collecting data:

Uniformly distributed array elements on a ring detector are numbered from 1 to N, where N is the number of array elements in the detector. A period of time before starting the collection, the detector is drawn by a motor for uniform motion (the direction of motion is defined as parallel to the Z-axis direction of a spatial three-dimensional direct coordinate system), and the speed is denoted as S. When the collection is started, appropriate delay is applied to $N_a$ selected array elements and ultrasonic waves are emitted, and are received by all N array elements. After a time interval T, the next group of $N_a$ selected array elements perform the same operation, and are received by all N array elements. Sequentially, after all emission events are completed, it cycles back to the first group of array elements to emit ultrasonic waves until a scanning area covers an imaging object, and scanning is stopped. Under such situation, one motion-emission cycle contains $N/N_a$ emission events, that is, $L=N/N_a$.

Figure 6:
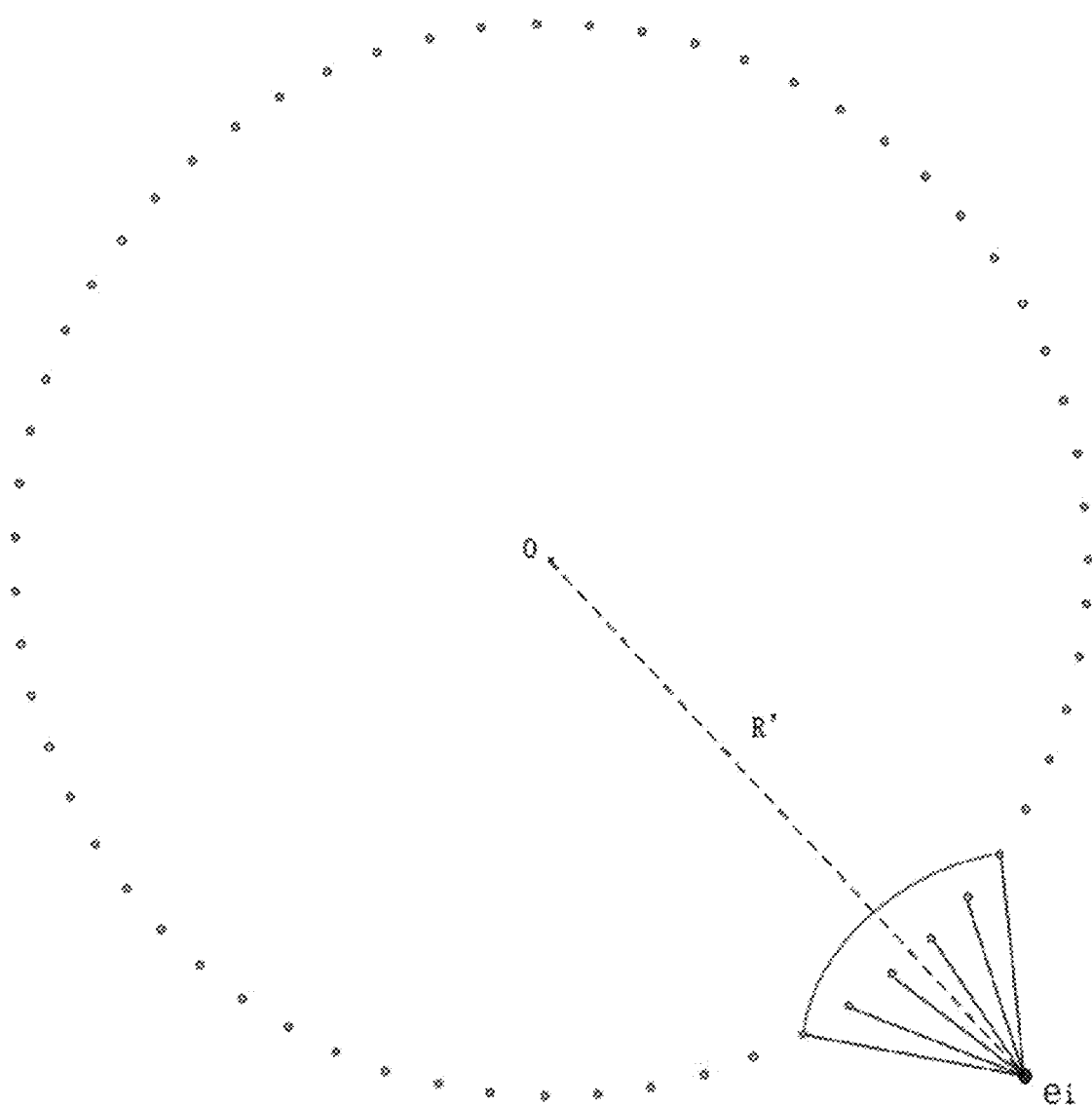
FIG. 6 is a schematic diagram of coordinate distribution of an emission event in Embodiment 4.
Figure 7:
FIG. 7 is a three-dimensional fetus shielding reconstruction result obtained by using Embodiment 2 of the disclosure.

In the embodiment, since each emission event corresponds to $N_a$ emission array element, the $N_a$ emission array element corresponds to one equivalent emission array element. The equivalent emission array element may be determined by a known manner in the prior art. As shown in FIG. 6, ei is the equivalent emission array element.

(2) Pre-processing the data:

A filtering process is performed on the raw echo data obtained in Step (1) to eliminate the direct current component and a part of the noise in the signal. A filtered data set is obtained for subsequent reconstruction in Step (5).

(3) Calculating the coordinates of each emission event:

As shown in FIG. 6, after an appropriate delay is applied to a group of array elements, the emitted spherical wavefront may be equivalent to a virtual array element emitting an ultrasonic wave (that is, the equivalent emission array element). At this time, the trajectory formed by all equivalent emission array elements is a spiral, and the radius thereof is greater than the radius of the detector and is denoted as R'. One emission cycle is referred as all array elements in the detector sequentially emitting once. It may be found that coordinates of corresponding array elements in two adjacent emission cycles satisfy the following relationship:

$x_{k+1,m} = x_{k,m}$ $y_{k+1,m} = y_{k,m}$ $z_{k+1,m} = z_{k,m}$ where ($x_{k,m}$, $y_{k,m}$, $z_{k,m}$) are the three-dimensional space coordinates of an array element assumed to be m in the k-th emission cycle, and $\Delta Z = L \times T \times S$ is the distance moved by the detector under the duration of one emission cycle.

Therefore, it is only necessary to calculate the coordinates of all equivalent emission array elements in one emission cycle, and the coordinates of the equivalent emission array elements in the remaining cycles may be derived from the above relationship. The plane where the N array elements of the ring detector are at is defined as parallel to an XOY plane of the three-dimensional direct coordinate system. The center of the ring detector moves along the Z-axis of the three-dimensional direct coordinate system, and three-dimensional space coordinates of the equivalent emission array element of the 1-st emission event in the first emission cycle are (R', 0, 0). The following shows that the space coordinates of all equivalent emission array elements in the first emission cycle satisfy:

$x_{1,m} = R \times \cos[(m-1) \times \Delta\theta]$ $y_{1,m} = R \times \sin[(m-1) \times \Delta\theta]$ $z_{1,m} = (m-1) \times T \times S$ where $$\Delta\theta = \frac{2\pi}{L}$$

is the central angle angular interval between adjacent equivalent emission array elements; and the value of m is from 1 to L.

(4) Performing voxelization on an imaging area:

Assuming that M emission cycles are actually required to cover the imaging object, then the imaging area may be limited to a cuboid with length, width, and height being respectively $2 \times R$, $2 \times R$, and $\Delta Z \times M$. At this time, since the actual radius of the ring-shaped probe is less than the radius of the area enclosed by the equivalent emission array element, the length and width of the imaging area are still $2 \times R$. The cuboid area is divided into $A \times A \times H$ voxels, that is, the imaging focus point.

(5) Performing synthetic aperture focusing on each of the imaging focus point:

Similar to FIG. 3, for a certain focus point P in the imaging area, the signal value of the point is given by the following formula:

$$I_p = \sum_{i=1}^{W} \sum_{j \in \Omega_i} s_{i,j}(t - \tau_{i,j})$$

where W is the total number of emission events in the overall scanning process, i corresponds to the emission element emitting at the i-th time (the emission element is also the equivalent emission element of the i-th emission event), and $\Omega_i$ is the set composed of sub-aperture receiving array elements corresponding to the i-th emission event. In the embodiment, $\Omega_i$ corresponds to the set constituting of receiving array elements that are symmetrically distributed at a connecting line between the equivalent emission array element and the center point of the ring-shaped probe and with the corresponding central angle not larger than 90° (the angle may be preset, as long as the angle does not exceed 90°, for example, the angle may be 90°). The array elements in the set mainly receive backscattered signals from the imaging object, are relatively close to the emission array element, and are used for reconstruction of a reflection image.

$$\tau_{i,j} = \frac{1}{c}(d_{i,TX} + d_{j,RX})$$

$$d_{i,TX} = \sqrt{(x_i - x_p)^2 + (y_i - y_p)^2 + (z_i - z_p)^2}$$

$$d_{j,RX} = \sqrt{(x_j - x_p)^2 + (y_j - y_p)^2 + (z_j - z_p)^2}$$

where $(x_i, y_i, z_i)$ are the three-dimensional space coordinates of the equivalent emission array element of the i-th emission event; $(x_j, y_j, z_j)$ are the three-dimensional space coordinates of a receiving array element when an array element numbered as j in the sub-aperture receiving array element set corresponding to the i-th emission event serves as the receiving array element; $(x_p, y_p, z_p)$ are the three-dimensional space coordinates of the imaging point P; $d_{i,TX}$ is the spatial distance between the equivalent emission array element of the i-th emission event and the imaging point P, and $d_{j,RX}$ is the spatial distance between a receiving array element and the imaging point P when an array element numbered as j in the sub-aperture receiving array element set corresponding to the i-th emission event serves as the receiving array element; c is the pre-selected sound speed value; $\tau_{i,j}$ is the delay time of a sound wave emitting from the emission element of the i-th emission event, passing through the imaging point P, and then reaching an array element numbered as j in the sub-aperture receiving array element set corresponding to the i-th emission event from the imaging point P when the element serves as the receiving array element; and $s_{i,j}(t-\tau_{i,j})$ represents the delay alignment echo signal received by an array element numbered as j in the sub-aperture receiving array element set corresponding to the i-th emission event when the element serves as the receiving array element.

c is a constant, and is the sound speed in the soft tissue, such as 1540 m/s.

(6) Post processing the data:

The post-processing of the focus result may mainly include steps such as filtering, envelope detection, logarithmic compression, and gray-scale mapping to implement the reconstruction of a three-dimensional ultrasound tomography image. The steps may be performed according to known processing manners in the prior art. For example:

Filtering: In order to reduce the impact of speckle noise on image quality in ultrasonic reflection imaging, a median filter may be used to process focus data. The size of the observation window is related to the number of focus points set.

Envelope detection: In medical ultrasound imaging, the main method used to obtain the signal envelope is to perform Hilbert transform on the signal, so as to obtain an analytical representation of the corresponding signal. The amplitude of the analytical signal is the desired envelope.

Logarithmic compression: Logarithmic operation is performed on the envelope signal to compress the dynamic range of the signal to an ideal range for display, which is generally adjusted to 50 to 70 dB.

Gray-scale mapping: The value of each focus point is linearly mapped to a gray-scale value of 0 to 255, that is, proportionally maps the weakest signal to 0 and the strongest signal to 255 for display in a display.

Finally, the reconstructed three-dimensional ultrasound tomography image may be imported into a three-dimensional reconstruction software for display.

Persons skilled in the art may easily understand that the above descriptions are only preferred embodiments of the disclosure and are not intended to limit the disclosure. Any modification, equivalent replacement, improvement, etc. made within the spirit and principle of the disclosure should be included in the protection scope of the disclosure.

What is claimed is:

1. A three-dimensional ultrasound tomography method based on spiral scanning, comprising:

Step (1) of collecting raw data, wherein:

array elements in a ring-shaped probe or a partial ring-shaped probe are numbered from 1 to N in a clockwise direction or a counterclockwise direction, where N is a total number of array elements in the probe, and the N array elements are uniformly distributed on the probe; under a premise that the probe maintains a uniform linear motion, an emission array element is switched according to a preset emission rule, and assuming that a motion-emission cycle contains L emission events, and each emission event corresponds to an equivalent emission array element, then the emission event numbered as 1 starts to emit an ultrasonic signal until the emission event numbered as L, and changes in trajectory with time of a position of the equivalent emission array element corresponding to each emission event in a three-dimensional space show a complete spiral or a partial spiral, so as to complete the motion-emission cycle; in this way, the emission array element is continuously updated to complete a plurality of motion-emission cycles; wherein for any emission event, while emitting the ultrasonic signal, each array element in the probe receives and collects the ultrasonic signal to obtain raw echo data;

Step (2) of pre-processing data, wherein:

a filtering process is performed on the raw echo data obtained in Step (1) to obtain a filtered signal;

Step (3) of calculating three-dimensional space coordinates of the equivalent emission array element of each emission event in each motion-emission cycle;

Step (4) of performing voxelization on an imaging area, wherein: voxelization is performed on a three-dimensional imaging area, and three-dimensional space coordinates of each imaging focus point are obtained;

Step (5) of performing synthetic aperture focusing on each of the imaging focus point, wherein: the three-dimensional space coordinates of the equivalent emission element of each emission event obtained in Step (3), and the three-dimensional space coordinates of each of the imaging focus point obtained in Step (4) are used, in the three-dimensional imaging area, based on a principle of synthetic aperture focusing technique, each voxel in the three-dimensional imaging area serves as the imaging focus point for focusing point by point, so as to obtain an echo intensity distribution of each of the imaging focus point; and based on the echo intensity distributions of the imaging focus points, the echo intensity distribution of the overall three-dimensional imaging area is obtained; and Step (6) of post-processing data, wherein: filtering, envelope detection, logarithmic compression, and gray-scale mapping are performed on the echo intensity distribution of the overall three-dimensional imaging area obtained in Step (5) to reconstruct a three-dimensional ultrasound tomography image, wherein Step (5) is specifically:

it is assumed that a total number of emission events is W, and the emission events are numbered from 1 to W, for a certain imaging focus point P in the three-dimensional imaging area, based on the principle of synthetic aperture focusing technique, obtaining the three-dimensional space coordinates of the equivalent emission array element of each emission event in Step (3), according to the three-dimensional space coordinates of the equivalent emission array element of a group of W emission events, the echo intensity distribution of the imaging focus point P is calculated, and the echo intensity distribution satisfies:

$$I_p = \sum_{i=1}^{W} \sum_{j \in \Omega_i} s_{i,j}(t - \tau_{i,j})$$

where i corresponds to an equivalent emission array element of an i-th emission event in the group of W emission events, $\Omega_i$ is a set composed of sub-aperture receiving array elements corresponding to the i-th emission event, and j represents an array element numbered as j in $\Omega_i$; and $$\tau_{i,j} = \frac{1}{c}(d_{i,TX} + d_{j,RX})$$

$$d_{i,TX} = \sqrt{(x_i - x_p)^2 + (y_i - y_p)^2 + (z_i - z_p)^2}$$

$$d_{j,RX} = \sqrt{(x_j - x_p)^2 + (y_j - y_p)^2 + (z_j - z_p)^2}$$

where $(x_i, y_i, z_i)$ are three-dimensional space coordinates of the equivalent emission array element of the i-th emission event $(x_j, y_j, z_j)$ are three-dimensional space coordinates of a receiving array element when the array element numbered as j in the sub-aperture receiving array element set corresponding to the i-th emission event serves as the receiving array element $(x_p, y_p, x_p)$ are three-dimensional space coordinates of the imaging point P; $d_{i,TX}$ is a spatial distance between the equivalent emission array element of the i-th emission event and the imaging point P, and $d_{j,RX}$ is a spatial distance between the receiving array element and the imaging point P when the array element numbered as j in the sub-aperture receiving array element set corresponding to the i-th emission event serves as the receiving array element c is a pre-selected sound speed value, preferably, c=1540 m/s; $T_{i,j}$ is a delay time of a sound wave starting from the equivalent emission element of the i-th emission event, passing through the imaging point P, and then reaching the array element numbered as j in the sub-aperture receiving array element set corresponding to the i-th emission event from the imaging point P when the element serves as the receiving array element $s_{i,j}(t-\tau_{i,j})$ represents a delay alignment echo signal received by the array element numbered as j in the sub-aperture receiving array element set corresponding to the i-th emission event when the element serves as the receiving array element.

2. The three-dimensional ultrasound tomography method based on spiral scanning according to claim 1, wherein the probe is a ring-shaped probe; and $\Omega_i$ corresponds to a section of continuous array element area on the ring-shaped probe, the area is bilaterally symmetrical with a connecting line between the equivalent emission array element corresponding to the i-th emission event and a center of the ring-shaped probe as an axis of symmetry, and a central angle formed by the area and the center of the ring-shaped probe does not exceed 90°.

3. The three-dimensional ultrasound tomography method based on spiral scanning according to claim 1, wherein in Step (1), the preset emission rule specifically corresponds to:
 (i) each emission event contains only one array element emitting an ultrasonic wave, and the array element corresponds to an equivalent emission array element; or
 (ii) each emission event contains a plurality of adjacent array elements simultaneously emitting ultrasonic waves, and the array elements together correspond to one equivalent emission array element; or
 (iii) each emission event contains a plurality of array elements emitting ultrasonic waves according to preset delay requirements, and the array elements together correspond to one equivalent emission array element.

4. The three-dimensional ultrasound tomography method based on spiral scanning according to claim 1, wherein in Step (1), when the probe is a ring-shaped probe, any one of the motion-emission cycles corresponds to a complete spiral; and
 when the probe is a partial ring-shaped probe, any one of the motion-emission cycles corresponds to a partial spiral.

5. The three-dimensional ultrasound tomography method based on spiral scanning according to claim 1, wherein in Step (2), the filtering process specifically removes a direct current component in the raw echo data.

6. A three-dimensional ultrasound tomography system based on spiral scanning, comprising:
 a raw data collection module, used to: number array elements in a ring-shaped probe or a partial ring-shaped probe from 1 to N in a clockwise direction or a counterclockwise direction, where N is a total number of array elements in the probe, wherein the N array elements are uniformly distributed on the probe; under a premise that the probe maintains a uniform linear motion, an emission array element is switched according to a preset emission rule, and assuming that a motion-emission cycle contains L emission events, and each emission event corresponds to an equivalent emission array element, then the emission event numbered as 1 starts to emit an ultrasonic signal until the emission event numbered as L, and changes in trajectory with time of a position of the equivalent emission array element corresponding to each emission event in a three-dimensional space show a complete spiral or a partial spiral, so as to complete the motion-emission cycle; in this way, the emission array element is continuously updated to complete a plurality of motion-emission cycles; wherein for any emission event, while emitting the ultrasonic signal, each array element in the probe receives and collects the ultrasonic signal to obtain raw echo data;
 a data pre-processing module, used to: filter the raw echo data to obtain a filtered signal;
 a three-dimensional space coordinate calculation module of the emission array element, used to: calculate three-dimensional space coordinates of the equivalent emission array element of each emission event in each motion-emission cycle;
 a three-dimensional space coordinate calculation module of an imaging focus point, used to: perform voxelization on a three-dimensional imaging area and obtain three-dimensional space coordinates of each imaging focus point; and an image reconstruction module, used to: use the three-dimensional space coordinates of the equivalent emission array element of each emission event and the three-dimensional space coordinates of each of the imaging focus point, wherein in the three-dimensional imaging area, based on a principle of synthetic aperture focusing technique, each voxel in the three-dimensional imaging area serves as the imaging focus point for focusing point by point, so as to obtain an echo intensity distribution of each of the imaging focus point; based on the echo intensity distributions of the imaging focus points, the echo intensity distribution of the overall three-dimensional imaging area may be obtained; and filtering, envelope detection, logarithmic compression, and gray-scale mapping are performed on the echo intensity distribution of the overall three-dimensional imaging area to reconstruct a three-dimensional ultrasound tomography image, wherein using the three-dimensional space coordinates of the equivalent emission array element of each emission event and the three-dimensional space coordinates of each of the imaging focus point includes:

it is assumed that a total number of emission events is W, and the emission events are numbered from 1 to W, for a certain imaging focus point P in the three-dimensional imaging area, based on the principle of synthetic aperture focusing technique, obtaining the three-dimensional space coordinates of the equivalent emission array element of each emission event, according to the three-dimensional space coordinates of the equivalent emission array element of a group of W emission events, the echo intensity distribution of the imaging focus point P is calculated, and the echo intensity distribution satisfies:

$$I_P = \sum_{i=1}^{W} \sum_{j \in \Omega_i} s_{i,j}(t - \tau_{i,j})$$

where i corresponds to an equivalent emission array element of an i-th emission event in the group of W emission events, $\Omega_i$ is a set composed of sub-aperture receiving array elements corresponding to the i-th emission event, and j represents an array element numbered as j in $\Omega_i$; and $$\tau_{i,j} = \frac{1}{c}(d_{i,TX} + d_{j,RX})$$
$$d_{i,TX} = \sqrt{(x_i - x_P)^2 + (y_i - y_P)^2 + (z_i - z_P)^2}$$
$$d_{j,RX} = \sqrt{(x_j - x_P)^2 + (y_j - y_P)^2 + (z_j - z_P)^2}$$

where $(x_i, y_i, z_i)$ are three-dimensional space coordinates of the equivalent emission array element of the i-th emission event $(x_j, y_j, z_j)$ are three-dimensional space coordinates of a receiving array element when the array element numbered as j in the sub-aperture receiving array element set corresponding to the i-th emission event serves as the receiving array element $(x_P, y_P, z_P)$ are three-dimensional space coordinates of the imaging point P; $d_{i,TX}$ is a spatial distance between the equivalent emission array element of the i-th emission event and the imaging point P, and $d_{j,RX}$ is a spatial distance between the receiving array element and the imaging point P when the array element numbered as j in the sub-aperture receiving array element set corresponding to the i-th emission event serves as the receiving array element c is a pre-selected sound speed value, preferably, c=1540 m/s; $\tau_{i,j}$ is a delay time of a sound wave starting from the equivalent emission element of the i-th emission event, passing through the imaging point P, and then reaching the array element numbered as j in the sub-aperture receiving array element set corresponding to the i-th emission event from the imaging point P when the element serves as the receiving array element $s_{i,j}(t-\tau_{i,j})$) represents a delay alignment echo signal received by the array element numbered as j in the sub-aperture receiving array element set corresponding to the i-th emission event when the element serves as the receiving array element.

* * * * *